United States Patent [19]

Anderson et al.

[11] Patent Number: 5,733,552
[45] Date of Patent: Mar. 31, 1998

[54] MOSQUITO REPELLING TECHNIQUE

[75] Inventors: William A. Anderson; Bill E. Brock, both of Glendale, Calif.

[73] Assignee: Garlic Research Labs, Glendale, Calif.

[21] Appl. No.: 654,666

[22] Filed: May 29, 1996

[51] Int. Cl.$^6$ .................................................... A61K 35/78
[52] U.S. Cl. ................................................................ 424/195.1
[58] Field of Search ........................ 424/195.1, DIG. 10

[56] References Cited

U.S. PATENT DOCUMENTS

| | | | |
|---|---|---|---|
| 4,455,304 | 6/1984 | Yaralian | 424/195.1 |
| 4,702,914 | 10/1987 | Ryan | 424/195.1 |
| 4,876,090 | 10/1989 | Wesler | 424/195.1 |
| 5,429,817 | 7/1995 | McKenzie | 424/195.1 |

OTHER PUBLICATIONS

USDA Research Adm. Bur of Entomology and Plant Quarantine, Plants of possible insecticidal value, N. E. McIndoo, p. 114, Allium Sativum L., May 1945.

Chem. Abstr., vol. 124, No. 17, (Columbus, OH, USA), p. 550, col. 1, the abstract No. 223670y, Dhar, et al., Effect of volatiles from neem and other natural products on gonotropic cycles and oviposition of Anopheles stephensi and An. culicifacies.J, Apr. 22, 1996.

*Primary Examiner*—Chhaya D. Sayala
*Attorney, Agent, or Firm*—G. Turner Moller

[57] ABSTRACT

Mosquitoes are discouraged from occupying a grassy recreational area by spraying dilute garlic juice on grass, shrubs and trees. Surprisingly, this treatment repels mosquitoes. More surprisingly, mosquitoes are repelled for many months. For reasons not wholly understood, mosquitoes are repelled by some component of garlic juice which may not be the odoriferous compounds. The equivalent of at least about 0.04 gallons of full strength garlic juice per acre is applied. Preferably, the garlic juice is applied in a concentration in the range of 0.04–0.5 gallons of full strength garlic juice per acre and in a strength of ½–5% garlic juice.

10 Claims, No Drawings

MOSQUITO REPELLING TECHNIQUE

This invention relates to a method for repelling mosquitoes, and more particularly to a method for repelling mosquitoes from grassy recreational areas.

BACKGROUND OF THE INVENTION

Although some species of mosquitoes are effective disease vectors, mosquitoes are mainly irritating pests. If one is trying to have some pleasant outdoor activity in the backyard, there is no simple, economical, unobjectionable technique to avoid mosquitoes.

There are basically two techniques: (1) burning citronella candles and (2) applying a repellent to the individual either by spraying or as a lotion. Citronella candles have many objections, such as being dependent on wind direction and having an odor easily detectable by humans. Lathering up with mosquito repellent isn't compatible with backyard barbeques, children's birthday parties or looking at the moon. Currently available mosquito repellents are better than mosquitoes but are tolerated only by people motivated to coexist with mosquitoes. Thus, most people opt for indoor entertainment during the mosquito season for want of an effective, unobjectionable repellent.

It is known to use garlic products as repellents for insects and birds as shown in U.S. Pat. Nos. 4,455,304; 4,876,090 and 5,429,817. Garlic juice has been sold to farmers and sprayed on field crops to control plant eating insects. It is known that dilute garlic oil is fatal to mosquito larvae. In parts of Africa, people eat garlic in the belief that the odor of garlic exuded through the skin acts as a repellant preventing Anopheles vectors from biting. It has been demonstrated that garlic fed to guinea pigs has a repellant effect on *Anopheles stephensi* but not *Aedes aegypti* mosquitoes.

Garlic juice is obtained by pressing garlic cloves. Garlic oil is allyl sulfide and is distilled garlic juice.

SUMMARY OF THE INVENTION

Garlic juice concentrate has been sold to farmers who spray a dilute solution on field crops to repel plant eating insects. Spraying is effective if done before the onset of substantial insect infestation. This technique is quite advantageous because the amount of garlic juice that is sprayed is economical, it does not repel beneficial insects that do not eat the plant and it does not have many of the other known objections to conventional pesticides such as water borne residues. The operative mechanism has always been thought to be that the plant incorporates some of the garlic juice, the insect eats part of the plant, doesn't like the garlic and either leaves the sprayed area or doesn't prosper for lack of food. Major evidence in support of this mechanism is that sprayed dilute garlic juice does not repel beneficial insects that do not eat the plant.

After many fields were sprayed, it slowly dawned that there was a reduction in resident mosquito population. This was surprising for a variety of reasons. First, mosquitoes are not normally thought to be plant eating insects and thus are not subject to the operative mechanism that repels plant eating insects. Thus, mosquitoes were not thought to be repelled any more than beneficial insects. Although mosquitoes are not a plant pest, investigation later showed that mosquitoes do ingest plant sap. Male mosquitoes do not bite to obtain a blood meal. Only female mosquitoes do and they bite only in the breeding cycle to obtain protein for offspring. Second, mosquitoes are repelled substantially immediately on spraying. There is insufficient time for the plant to incorporate the garlic juice, have the mosquito suck sap from the plant to contact the garlic and thereby be repelled. Thus, some other mechanism must be operating. Observation and investigation suggest there is some compound in garlic that mosquitoes find offensive and can detect without ingesting it, presumably by smell.

In this invention, a dilute mixture of garlic juice and water is applied in a grassy area where recreational activities are to take place. Typical sites for use of this invention are in the yard around one's home or apartment, on a golf course, around a race track, in a campground, in a park, on a baseball or football field, and the like. In a few hours, the characteristic garlic odor dissipates and can no longer be detected by humans. For reasons which are not wholly understood, mosquitoes vacate areas where garlic juice has been sprayed. More surprisingly and more importantly, mosquitoes stay away from sprayed areas for several months for reasons which can only be speculated about.

The garlic juice is preferably applied by spraying. The quantity of garlic juice delivered can vary substantially but it is at least 0.04 equivalent gallons of full strength garlic juice per acre and is normally in the range of 0.04–0.5 gallons per acre. The garlic juice is sprayed over the entire area to be protected. Preferably, the garlic juice is sprayed in a pattern designed to herd mosquitoes into an unsprayed area where a resident mosquito population is less irritating.

It is an object of this invention to provide an improved technique for repelling mosquitoes from grassy areas.

It is an object of this invention to provide an improved technique for repelling mosquitoes from grassy recreational areas.

Another object of this invention is to provide a simple and inexpensive way of repelling mosquitoes by spraying dilute garlic juice on grass, shrubs and trees.

These and other objects of this invention will become more fully apparent as this description proceeds, reference being made to the accompanying drawings and appended claims.

DETAILED DESCRIPTION

This invention is a technique for repelling mosquitoes from grassy recreational areas. As used herein, a grassy recreational area is a place where a common existing plant is a ground covering grass, such as native grasses, Bermuda, St. Augustine, Zoyzia and the like. Grassy areas may also include shrubs, trees and flowers in abundance. A recreational area is a place where recreation occurs or is intended to occur, such as one's backyard, a sports field, a golf course, a race track, a campground or the like and is readily distinguished from cropland.

Repelling mosquitoes is accomplished by applying a garlic extract on locales where mosquitoes normally rest, such as on grass, shrubs, trees, flowers and the like. Surprisingly, mosquitoes do not like some component of garlic and leave. Also surprisingly, mosquitoes stay away from sprayed areas for extended periods of time, measured in months.

Garlic comprises a high concentration of sulphur compounds, only some of which contribute to its characteristic odor. Although the odor causing compounds may be the effective agent to repel mosquitoes, this is not known to be true and arguments exist which point to less odoriferous compounds as being the effective materials in this invention. Odor causing compounds are normally thought to be volatile which necessarily means they evaporate and thus have short lived effects. Because the treatment of this invention repels mosquitoes for many months, one of two things must be true: (1) mosquitoes can detect far smaller concentrations of volatile garlic compounds than humans or (2) it is not the odor causing, volatile components that repel mosquitoes. At the present state of knowledge, one can only say that garlic, spread over the normal resting places of mosquitoes, repels them for several months.

The preferred garlic extract is garlic juice obtained by pressing garlic cloves that have been machine cleaned of husks, stems, dirt and the like. The garlic juice is filtered to remove any suspended pulp and then typically diluted with clear water to provide a concentrate which is 10% garlic juice, 90% water. The water is preferably deionized or reverse osmosis water. Simple concentrates tend to deteriorate over time, so any suitable preservative such as citric acid, sodium benzoate or potassium sorbate may be added. The concentrate is normally bottled and shipped.

The duration of the treatment of this invention depends on a wide variety of factors, which are believed to be not wholly appreciated. Common sense suggests that high wind and/or heavy rain reduces the concentration of the effective components and thus lessens the duration of effectiveness. While this is undoubtedly true, the duration of effectiveness is still surprisingly long. One would not expect a treatment of this invention to survive a torrential rain but anecdotal reports show that it has.

The concentration of garlic juice applied to the grassy recreational areas may vary, depending on the intended duration of effectiveness, the desire for certain results and the effect of anticipated climatic conditions, such as wind and rain. The garlic juice should be applied in an amount of at least 0.04 equivalent full strength gallons per acre and is normally in the range of 0.04–0.5 full strength gallons per acre. This is the equivalent of at least 0.4 gallons of 10% juice concentrate per acre or the equivalent of 0.4–5 gallons of 10% juice concentrate per acre. This is conveniently accomplished by diluting the concentrate, in a conventional sprayer, at a 10:1 ratio and spraying at least 4 gallons of 1% solution per acre.

There is obviously some minimum concentration below which a garlic juice spray is ineffective to repel mosquitoes. Present indications are that less than about 4 gallons of 1% solution per acre is ineffective. The maximum concentration of sprayed garlic juice appears to be dictated more by economics than science, i.e. it is wasteful to spray much over 50 gallons of 1% garlic juice when repelling mosquitoes.

It is convenient to spray a nominally 1% solution of garlic juice because it is convenient to ship a 10% concentrate and dilution sprayers are readily available. It turns out that a 1% solution is also desirable because it is so dilute that it will not burn plants. Solutions above about 5% garlic juice will burn plants quite easily. Solutions below about ½% may be so dilute as to be less effective in repelling mosquitoes. It is accordingly preferred that the sprayed solution be in the range of ½–5% garlic juice.

The dilute garlic juice should be sprayed to thoroughly wet all normal resting places of mosquitoes, such as grass, shrubs, trees and flowers. Trees should be sprayed as far up in the foliage as the user can conveniently reach. It is preferred to spray in the early morning or late afternoon. Spraying is preferably done in a large area, within practical limits, around the location desired to be protected from mosquitoes. For example, if it is desired to repel mosquitoes from a patio area of a typical suburban home, it is desirable to spray the entire yard. At the other extreme, if it is desired to repel mosquitoes from a golf course, it is sufficient to spray the golf course but not the neighborhood around it.

When spraying large areas, such as golf courses, campgrounds, race tracks, playing fields and the like, it is much preferred to spray just prior to the onset of the mosquito season. It is known that dilute garlic oil is fatal to mosquito larvae. It has be found that dilute garlic juice is also fatal to mosquito larvae. By spraying early in the season and spraying any casual water or ponds, the dilute garlic juice kills much of the larvae so the adult mosquito population is much reduced and thus much easier to contend with.

The following tests were conducted in grassy recreational areas to demonstrate the effectiveness of this invention. Spray volume applications of ten to twenty gallons of approximately 1% garlic juice per acre were made either in early morning or late afternoon with little or no wind present and with no rain in the forecast for at least forty eight hours. In these tests, the top and underside of foliage was sprayed.

The effectiveness of this invention was determined by counting the number of mosquitoes that landed on the bare arm of a human test subject before and after treatment. The landing counts used to evaluate the mosquito population were taken over a one minute period beginning immediately after a five minute waiting period. In general, the control area was selected to be similar to the treated area and to be at least 10,000 square feet in size and at least about 200 feet away from the treated area. Visual sightings were also conducted in conjunction with the land rate counts inside and outside the treated areas to provide a useful index.

Test 1

Thirty acres of a golf course in Burleigh, N. Dak. were sprayed beginning in the early morning when the temperature was 65° F., the sky was cloudy, humidity was 59% and the wind was 1 mph. During the eight week test period, it rained periodically. A substantial mosquito infestation existed and the area was heavily wooded with an extreme climate range. A minimum of ten gallons per acre and a maximum of twenty gallons per acre of a nominal 1% garlic juice solution was sprayed with a boom sprayer. The base count is the landing count prior to treatment.

| Area | Base Count | Landing Count Number of Weeks Following Treatment | | | | | | | |
|---|---|---|---|---|---|---|---|---|---|
| | | 1 | 2 | 3 | 4 | 5 | 6 | 7 | 8 |
| treated | 27 | 1 | 1 | 0 | 1 | 3 | 1 | 1 | 2 |
| untreated, i.e. control | 31 | 35 | 9 | 19 | 29 | 30 | 26 | 18 | 24 |

Test 2

Three acres of a golf course, clubhouse with an open deck surrounded by shrubs, trees, turf and a driving range in Farmington Falls, Me. were sprayed beginning in the early morning when the temperature was 59° F., the sky was partly cloudy, humidity was 58% and the wind was 2 mph. A mosquito infestation existed, a river ran through the site and the area experienced a northern climate. During the eight week test period, heavy rains were experienced. A minimum of ten gallons per acre and a maximum of twenty gallons per acre of a nominal 1% garlic juice solution was sprayed with a hand held sprayer. The base count is the landing count prior to treatment.

|      | Landing Count |   |   |   |   |   |   |   |   |
|------|------|---|---|---|---|---|---|---|---|
|      | Base | Number of Weeks Following Treatment | | | | | | | |
| Area | Count | 1 | 2 | 3 | 4 | 5 | 6 | 7 | 8 |
| treated | 27 | 1 | 1 | 1 | 0 | 1 | 1 | 2 | 2 |
| untreated, i.e. control | 24 | 26 | 19 | 5 | 17 | 15 | 12 | 20 | 17 |

Test 3

A one hundred ninety acre horse race track with a large number of ornamentals and trees in Salem, N.H. was sprayed beginning in the early morning when the temperature was 67° F. the sky was partly cloudy, humidity was 65% and the wind was 3 mph. The area was infested with mosquitoes, there were numerous bodies of water and race horses were on the site. During the eight week test period, no rain fell. A minimum of ten gallons per acre and a maximum of twenty gallons per acre of a nominal 1% garlic juice solution was sprayed with a tractor sprayer and jet packs. The base count is the landing count prior to treatment.

|      | Landing Count |   |   |   |   |   |   |   |   |
|------|------|---|---|---|---|---|---|---|---|
|      | Base | Number of Weeks Following Treatment | | | | | | | |
| Area | Count | 1 | 2 | 3 | 4 | 5 | 6 | 7 | 8 |
| treated | 16 | 1 | 1 | 1 | 1 | 1 | 1 | 1 | 1 |
| untreated, i.e. control | 21 | 24 | 29 | 16 | 27 | 25 | 14 | 18 | 23 |

Test 4

A ⅔ acre golf driving range in Hermitage, Pa. was sprayed beginning in the early morning when the temperature was 68° F., the sky was clear, humidity was 59% and the wind was 2 mph. During the eight week test period, no rain fell. A minimum of ten gallons per acre and a maximum of twenty gallons per acre of a nominal 1% garlic juice solution was sprayed with hand held sprayers. The base count is the landing count prior to treatment.

|      | Landing Count |   |   |   |   |   |   |   |   |
|------|------|---|---|---|---|---|---|---|---|
|      | Base | Number of Weeks Following Treatment | | | | | | | |
| Area | Count | 1 | 2 | 3 | 4 | 5 | 6 | 7 | 8 |
| treated | 22 | 0 | 1 | 2 | 0 | 1 | 0 | 2 | 1 |
| untreated, i.e. control | 23 | 29 | 19 | 30 | 9 | 20 | 26 | 14 | 19 |

Test 5

A one acre golf course with clubhouse surrounded by ornamentals, tall shrubs and trees in Orchard Lake, Mich. was sprayed beginning in the middle afternoon when the temperature was 83° F., the sky was partly cloudy, humidity was 72% and the wind was 7 mph. During the eight week test period, no rain fell. A minimum of ten gallons per acre and a maximum of twenty gallons per acre of a nominal 1% garlic juice solution was sprayed with a boom sprayer. The base count is the landing count prior to treatment.

|      | Landing Count |   |   |   |   |   |   |   |   |
|------|------|---|---|---|---|---|---|---|---|
|      | Base | Number of Weeks Following Treatment | | | | | | | |
| Area | Count | 1 | 2 | 3 | 4 | 5 | 6 | 7 | 8 |
| treated | 22 | 0 | 1 | 2 | 0 | 1 | 0 | 2 | 1 |
| untreated, i.e. control | 23 | 29 | 19 | 30 | 9 | 20 | 26 | 14 | 19 |

Test 6

A fifty five acre heavily wooded golf course with two small ponds on the edge of a lake in Shakopee, Minn. was sprayed beginning in the early morning when the temperature was 64° F., the sky was partly cloudy, humidity was 68% and the wind was 2 mph. During the eight week test period, no rain fell. A minimum of ten gallons per acre and a maximum of twenty gallons per acre of a nominal 1% garlic juice solution was sprayed with a tractor boom sprayer and jet pack. The base count is the landing count prior to treatment.

|      | Landing Count |   |   |   |   |   |   |   |   |
|------|------|---|---|---|---|---|---|---|---|
|      | Base | Number of Weeks Following Treatment | | | | | | | |
| Area | Count | 1 | 2 | 3 | 4 | 5 | 6 | 7 | 8 |
| treated | 29 | 0 | 2 | 2 | 1 | 1 | 1 | 2 | 2 |
| untreated, i.e. control | 31 | 19 | 26 | 24 | 21 | 15 | 20 | 11 | 21 |

Test 7

A 1500 square foot residential lawn with ornamentals and evergreens in Los Angeles, Calif. was sprayed beginning in the early evening when the temperature was 76° F., the sky was clear,. humidity was 68% and the wind was 9 mph. During the eight week test period, no rain fell. A mosquito infestation existed in this coastal environment with low mountains and hills. A minimum of ten gallons per acre and a maximum of twenty gallons per acre of a nominal 1% garlic juice solution was sprayed with a hand held sprayer. The base count is the landing count prior to treatment.

|      | Landing Count |   |   |   |   |   |   |   |   |
|------|------|---|---|---|---|---|---|---|---|
|      | Base | Number of Weeks Following Treatment | | | | | | | |
| Area | Count | 1 | 2 | 3 | 4 | 5 | 6 | 7 | 8 |
| treated | 12 | 0 | 0 | 1 | 2 | 0 | 1 | 0 | 0 |
| untreated, i.e. control | 10 | 11 | 8 | 12 | 10 | 45 | 7 | 9 | 6 |

Test 8

A 31 acre campground with 700 mostly cottonwood trees and a wide variety of shrubs, grassy areas and camping equipment in Interior, S. Dak. was sprayed beginning the early morning when the temperature was 63° F., the sky was clear, humidity was 58% and the wind was 3 mph. During the eight week test period, no rain fell. A mosquito infestation existed in this area bordering a river. A minimum of ten gallons per acre and a maximum of twenty gallons per acre of a nominal 1% garlic juice solution was sprayed with a hand held sprayer. The base count is the landing count prior to treatment.

| Area | Base Count | Landing Count Number of Weeks Following Treatment | | | | | | | |
|---|---|---|---|---|---|---|---|---|---|
| | | 1 | 2 | 3 | 4 | 5 | 6 | 7 | 8 |
| treated | 28 | 0 | 1 | 1 | 2 | 1 | 0 | 1 | 1 |
| untreated, i.e. control | 21 | 19 | 22 | 31 | 18 | 20 | 23 | 17 | 19 |

Test 9

A ⅔ acre private residence with numerous shrubs, trees, lawns, landscaping, flower beds in Youngstown, New York was sprayed beginning the late afternoon when the temperature was 78° F., the sky was partly cloudy, humidity was 73% and the wind was 6 mph. During the eight week test period, no rain fell. A mosquito infestation existed in this area bordering the Niagara River and Lake Ontario. A minimum of ten gallons per acre and a maximum of twenty gallons per acre of a nominal 1% garlic juice solution was sprayed with a garden hose sprayer. The base count is the landing count prior to treatment.

| Area | Base Count | Landing Count Number of Weeks Following Treatment | | | | | | | |
|---|---|---|---|---|---|---|---|---|---|
| | | 1 | 2 | 3 | 4 | 5 | 6 | 7 | 8 |
| treated | 28 | 1 | 1 | 1 | 2 | 1 | 2 | 1 | 1 |
| untreated, i.e. control | 31 | 27 | 24 | 13 | 22 | 19 | 21 | 28 | 17 |

Test 10

A one acre private lake front property in Bloomfield Hills, Mich. was sprayed. The test area was about one-third covered with ground cover and the balance was a sand beach. A landscaped yard surrounded the residence. Spraying began in early evening when the temperature was 72° F., the sky was cloudy, humidity was 70% and the wind was 5 mph. During the eight week test period, no rain fell. A mosquito infestation existed in this area. A minimum of ten gallons per acre and a maximum of twenty gallons per acre of a nominal 1% garlic juice solution was sprayed with a garden hose sprayer. The base count is the landing count prior to treatment.

| Area | Base Count | Landing Count Number of Weeks Following Treatment | | | | | | | |
|---|---|---|---|---|---|---|---|---|---|
| | | 1 | 2 | 3 | 4 | 5 | 6 | 7 | 8 |
| treated | 28 | 1 | 2 | 1 | 1 | 0 | 1 | 2 | 1 |
| untreated, i.e. control | 36 | 22 | 34 | 19 | 27 | 12 | 22 | 17 | 19 |

Test 11

A twenty acre tract adjacent a private residence in Balch Springs, Tex. was sprayed. The test area included tall grasses, weeds, shrubs and trees. Spraying began in early morning when the temperature was 62° F. the sky was clear, humidity was 67% and the wind was 4 mph. During the eight week test period, no rain fell. A mosquito infestation existed in this area which was near a metropolitan area in hilly terrain with hot summers. A minimum of ten gallons per acre and a maximum of twenty gallons per acre of a nominal 1% garlic juice solution was sprayed with a garden hose sprayer. The base count is the landing count prior to treatment.

| Area | Base Count | Landing Count Number of Weeks Following Treatment | | | | | | | |
|---|---|---|---|---|---|---|---|---|---|
| | | 1 | 2 | 3 | 4 | 5 | 6 | 7 | 8 |
| treated | 28 | 0 | 1 | 1 | 2 | 0 | 2 | 0 | 1 |
| untreated, i.e. control | 24 | 12 | 19 | 18 | 17 | 14 | 9 | 16 | 8 |

Test 12

A one-eighth acre private residence in Fernandina Beach, Fla. was sprayed. The test area included subtropic ornamentals numerous trees and a landscaped lawn area. Spraying began in early evening when the temperature was 79° F., the sky was cloudy, humidity was 80% and the wind was 5 mph. Two days after treatment, it rained and periodic rain occurred during the eight week test period. A mosquito infestation existed in this area which has hot stormy summers with level terrain adjacent the ocean. A minimum of ten gallons per acre and a maximum of twenty gallons per acre of a nominal 1% garlic juice solution was sprayed with a garden hose sprayer. The base count is the landing count prior to treatment.

| Area | Base Count | Landing Count Number of Weeks Following Treatment | | | | | | | |
|---|---|---|---|---|---|---|---|---|---|
| | | 1 | 2 | 3 | 4 | 5 | 6 | 7 | 8 |
| treated | 29 | 1 | 0 | 1 | 1 | 1 | 2 | 0 | 1 |
| untreated, i.e. control | 31 | 28 | 27 | 18 | 21 | 26 | 15 | 18 | 21 |

It is apparent that adult mosquitoes were immediately repelled from the test areas. The effectiveness continued for at least two months after one treatment of dilute garlic juice. There were no indications of adverse effects from use of the invention at any test site. The garlic odor disappeared from the test areas shortly after treatment, usually less than thirty minutes.

Although this invention has been disclosed and described in its preferred forms with a certain degree of particularity, it is understood that the present disclosure of the preferred forms is only by way of example and that numerous changes may be resorted to without departing from the spirit and scope of the invention as hereinafter claimed.

I claim:

1. A method of repelling mosquitoes from a grassy recreational area comprising applying to the grassy recreational area a dilute liquid garlic extract, the liquid garlic extract being in an amount equivalent to at least 0.4 gallons of 10% garlic juice concentrate per acre and repelling mosquitoes from the grassy recreational area for at least several weeks in response to the dilute garlic extract.

2. The method of claim 1 wherein the grassy area includes shrubs and the applying step comprises applying the dilute garlic extract to the shrubs.

3. The method of claim 1 wherein the grassy area includes trees and the applying step comprises applying the dilute garlic extract to the trees.

4. The method of claim 1 wherein the grassy area includes flowers and the applying step comprises applying the dilute garlic extract to the flowers.

5. The method of claim 1 wherein the dilute garlic extract is in a concentration of 0.04–0.5 gallons of full strength garlic juice per acre.

6. The method of claim 1 wherein the dilute garlic extract is dilute garlic juice and the applying step comprises spraying thee dilute garlic juice onto the grassy recreational area in a concentration of about ½–5% garlic juice.

7. The method of claim 6 wherein the concentration is about 1% garlic juice.

8. The method of claim 1 wherein the dilute garlic extract is a solution of 10% garlic juice, trace preservative, balance water and wherein the applying step comprises adding water to the dilute garlic extract to produce a solution of about ½–5% garlic juice and then spraying the ½–5% garlic juice solution onto the grassy recreational area.

9. The method of claim 8 wherein the solution is about 1% garlic juice.

10. The method of claim 1 wherein the mosquitoes are repelled for at least eight weeks.

* * * * *